(12) United States Patent
Fischer et al.

(10) Patent No.: US 9,011,425 B2
(45) Date of Patent: Apr. 21, 2015

(54) ABLATION SYSTEM

(75) Inventors: Gerald Fischer, Völs (AT); Florian Hintringer, Ampass (AT)

(73) Assignee: Afreeze GmbH, Innsbruck (AT)

( * ) Notice: Subject to any disclaimer, the term of this patent is extended or adjusted under 35 U.S.C. 154(b) by 1256 days.

(21) Appl. No.: 12/922,157

(22) PCT Filed: Mar. 12, 2009

(86) PCT No.: PCT/EP2009/001804
§ 371 (c)(1),
(2), (4) Date: Dec. 8, 2010

(87) PCT Pub. No.: WO2009/112269
PCT Pub. Date: Sep. 17, 2009

(65) Prior Publication Data
US 2011/0106070 A1    May 5, 2011

Related U.S. Application Data

(60) Provisional application No. 61/035,865, filed on Mar. 12, 2008.

(51) Int. Cl.
*A61B 18/02*    (2006.01)
*A61B 18/14*    (2006.01)
(Continued)

(52) U.S. Cl.
CPC .............. *A61B 18/02* (2013.01); *A61B 18/1492* (2013.01); *A61B 18/18* (2013.01); *A61B 18/20* (2013.01); *A61B 2017/00867* (2013.01); *A61B 2018/00273* (2013.01); *A61B 2018/00279* (2013.01); *A61B 2018/00285* (2013.01); *A61B 2018/00351* (2013.01); *A61B 2018/00375* (2013.01); *A61B 2018/00577* (2013.01); *A61B 2018/00916* (2013.01); *A61B 2018/0212* (2013.01)

(58) Field of Classification Search
USPC ........................................... 606/21, 41
See application file for complete search history.

(56) References Cited

U.S. PATENT DOCUMENTS 5,676,693 A    10/1997    LaFontaine
5,687,723 A *  11/1997    Avitall ........................ 600/374
(Continued)

FOREIGN PATENT DOCUMENTS

EP    1 127 552 A1    8/2001
EP    1 356 779 A1    10/2003
(Continued)

OTHER PUBLICATIONS

International Search Report, dated Sep. 30, 2009, Corresponding to PCT/EP2009/001804.
(Continued)

*Primary Examiner* — Joseph Stoklosa
*Assistant Examiner* — Jocelyn D Ram
(74) *Attorney, Agent, or Firm* — Christie, Parker & Hale, LLP

(57) ABSTRACT

An ablation device comprising a positioning catheter adapted to be positionable in a heart and comprising a fixation mechanism for fixing the positioning catheter in the heart, and an ablation catheter adapted to ablate material of the heart using the ablation catheter, wherein the ablation catheter is designed to ablate tissue along an isthmus of the heart, wherein the positioning catheter and the ablation catheter are provided to be movable relative to one another.

20 Claims, 9 Drawing Sheets

(51) Int. Cl.
*A61B 18/18* (2006.01)
*A61B 18/20* (2006.01)
*A61B 17/00* (2006.01)
*A61B 18/00* (2006.01)

(56) References Cited

U.S. PATENT DOCUMENTS

| | | | |
|---|---|---|---|
| 5,800,428 | A | 9/1998 | Nelson et al. |
| 5,876,399 | A | 3/1999 | Chia et al. |
| 5,906,612 | A * | 5/1999 | Chinn ............... 606/20 |
| 6,071,279 | A * | 6/2000 | Whayne et al. ............... 606/41 |
| 6,235,019 | B1 | 5/2001 | Lehmann et al. |
| 6,241,722 | B1 | 6/2001 | Dobak et al. |
| 6,325,797 | B1 * | 12/2001 | Stewart et al. ............... 606/41 |
| 6,540,740 | B2 | 4/2003 | Lehmann et al. |
| 6,602,247 | B2 | 8/2003 | Lalonde |
| 6,629,972 | B2 | 10/2003 | Lehmann et al. |
| 6,899,709 | B2 | 5/2005 | Lehmann et al. |
| 2001/0021867 | A1 | 9/2001 | Kordis et al. |
| 2001/0031942 | A1 | 10/2001 | Tollner et al. |
| 2002/0111618 | A1 | 8/2002 | Stewart et al. |
| 2003/0204186 | A1 * | 10/2003 | Geistert ............... 606/41 |
| 2003/0204187 | A1 * | 10/2003 | Hintringer et al. ............... 606/41 |
| 2004/0034347 | A1 | 2/2004 | Hall et al. |
| 2005/0065420 | A1 * | 3/2005 | Collins et al. ............... 600/374 |
| 2006/0009752 | A1 * | 1/2006 | Lehmann et al. ............... 606/21 |
| 2010/0057073 | A1 * | 3/2010 | Roman et al. ............... 606/33 |
| 2010/0057074 | A1 * | 3/2010 | Roman et al. ............... 606/33 |

FOREIGN PATENT DOCUMENTS

| | | |
|---|---|---|
| WO | WO 99/22658 | 5/1999 |
| WO | WO 2006/010908 A1 | 2/2006 |

OTHER PUBLICATIONS

International Preliminary Report on Patentability, dated Sep. 14, 2010, corresponding to PCT/EP2009/001804, 9 pages.

* cited by examiner

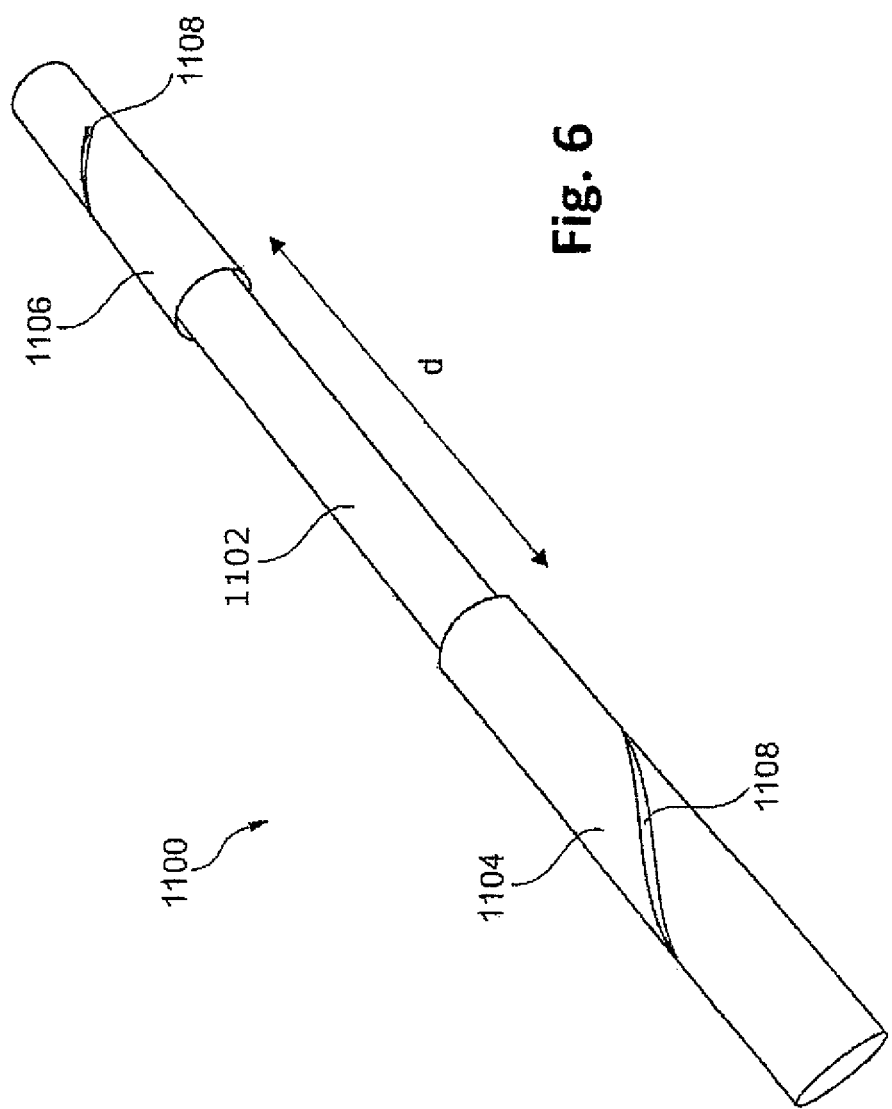

ABLATION SYSTEM

CROSS-REFERENCE TO A RELATED APPLICATION

This application is a National Phase Patent Application of International Patent Application Number PCT/EP2009/001804, filed on Mar. 12, 2009, which claims priority of U.S. Provisional Application No. 61/035,865, filed on Mar. 12, 2008.

This application claims the benefit of the filing date of U.S. Provisional Patent Application No. 61/035,865 filed Mar. 12, 2008, the disclosure of which is hereby incorporated herein by reference.

The invention relates to an ablation device.

Moreover, the invention relates to a method of operating an ablation device.

Furthermore, the invention relates to an ablation element for an ablation device.

Many cardiac arrhythmias can be treated by selectively blocking pathways or sources of electrical activation in the myocardial tissue by catheter ablation. The application of an ablation medium (radio-frequency current, extreme cold, ultra-sound, laser, etc.) triggers cell death of electrically conducting myocytes and the formation of a non-conducting lesion.

Cryosurgery is the application of extreme cold to ablate abnormal or diseased tissue. Cryosurgery works by taking advantage of the destructive force of freezing temperatures on cells. At low temperatures, ice crystals may form inside the cells, which can tear them apart. More damage may occur when blood vessels supplying the tissue freeze.

EP 1,356,779 discloses a device which has a catheter with a counter bearing device near its distal end for holding the distal end on a cardial vessel opening, a linear ablation applicator arranged on the proximal or distal side of the counter bearing and able to be changed from a stretched passive position to a radially expanded, approximately circular peripheral ablation position.

In some applications an elongated lesion has to be created in an isthmus structure of the heart. For example in patients with right atrial flutter, the propagation of the activation pulse in the isthmus between the inferior caval vein and the tricuspid valve is blocked by catheter ablation. In current clinical practice this ablation line is typically created by a point by point creation of essentially focal lesions using a state of the art ablation medium (radio frequency alternating current, cryoablation, laser, etc.). Another example for the ablation of an isthmus structure is described in US 2003/0204186. Here the isthmus between two pulmonary veins in the left atrium is ablated for treating atrial fibrillation.

U.S. Pat. No. 5,676,693, U.S. Pat. No. 5,800,428 and EP 1,127,552 disclose devices which enable the creation of elongated lesions using an electrical current source as ablation medium. Devices for creating elongated lesions by cryoablation are disclosed in U.S. Pat. No. 6,235,019, U.S. Pat. No. 6,241,722, U.S. Pat. No. 6,540,740, U.S. Pat. No. 6,602,247, U.S. Pat. No. 6,629,972 and U.S. Pat. No. 6,899,709.

U.S. Pat. No. 6,629,972 discloses a cryogenic catheter which includes an outer flexible member having at least one cryogenic fluid path through the flexible member. The at least one fluid path is defined by a plurality of flexible members disposed within the outer flexible member.

It is an object of the invention to provide an efficient ablation system.

In order to achieve the object defined above, an ablation device, a method of operating an ablation device, and an ablation element according to the independent claims are provided.

According to an exemplary embodiment of the invention, an ablation device (for instance for cyroablation/cryosurgery) is provided, the ablation device comprising a positioning catheter adapted to be positionable in a heart (for instance of a human or an animal such as a mammalian) and comprising a fixation mechanism (such as an inflatable balloon or a screw mechanism for anchoring a part of the device in heart tissue) for fixing the positioning catheter in the heart, and an ablation catheter adapted to ablate tissue of the heart using the ablation catheter, wherein the ablation catheter is designed to selectively (particularly with a proper spatial resolution for distinguishing portions of the heart to be ablated from portions of the heart to be not ablated) ablate tissue along an isthmus of the heart. The positioning catheter and the ablation catheter may be provided to be movable relative to one another (for instance by a translational motion or a screwing motion; one of the catheters may remain fixed whereas the other one of the catheters may be moved).

According to another exemplary embodiment of the invention, a method of operating an ablation device is provided, the method comprising positioning a positioning catheter of the ablation device in a heart and fixing the positioning catheter in the heart by a fixation mechanism, and ablating tissue selectively along an isthmus of the heart using an ablation catheter of the ablation device, wherein the operating comprises moving the positioning catheter and the ablation catheter relative to one another.

According to still another exemplary embodiment of the invention, an ablation element for an ablation device (for instance, but not exclusively, for an ablation device having the above mentioned features) is provided, the ablation element comprising a tubular body defining an inner lumen (which may be sealed to prevent fluid communication between the inner lumen and an outer environment of the ablation element), wherein the tubular body comprises a core (particularly an inner tubular body portion) formed by a wound filament structure and comprises a mantle (particularly an outer tubular body portion) surrounding the core, wherein the tubular body, particularly the mantle, is configured to have a spatially varying value of thermal conductivity (or heat conductivity or thermal coupling) along a circumference (i.e. along an outer perimeter) of the tubular body.

According to yet another exemplary embodiment of the invention, an ablation device is provided, the ablation device comprising an ablation element having the above mentioned features and being adapted for ablating a defined portion of an object (for instance of a human heart) upon supply of an ablation medium (for instance cooling energy obtained from an essentially isenthalpically expanded cooling fluid such as nitrous oxide) to the ablation element by an ablation source.

The term "catheter" may particularly denote a tube that can be inserted into a body cavity, duct or vessel. Catheters may thereby allow access by surgical instruments. A catheter may be a flexible tube. In other embodiments, a catheter may be a rigid tube. Its diameter may vary particularly between 0.3 mm and 10 mm.

The term "ablation device" may particularly denote any apparatus which is adapted to ablate, deactivate, destroy or remove material, particularly tissue of a physiological object such as a human being or an animal, via the application of an ablation medium such as extreme cold or heat.

The term "object" may particularly denote any object under examination, analysis or ablation and may be a human being or an animal. More particularly, it may be an organ of such a physiological object, particularly a heart or a part thereof, for instance the isthmus. The object may be a body under investigation which may particularly denote any human being, any animal, and any plant (any organism). It may be a living body so that living tissue may be investigated or processed.

The term "tubular body" may particularly denote a (for instance oblong) hollow structure having any desired geometry and having a lumen (i.e. a cavity or a passageway, capable of receiving and conducting a fluid and/or members) of any desired shape, such as a lumen having a cylindrical, oval, or polygonal cross-section.

The term "ablating tissue selectively along an isthmus" may particularly denote that a shape, a dimension and a geometry of an ablation element/catheter is specifically designed so that material of the anatomically shaped isthmus of the heart can be made subject of an ablation procedure, whereas material which does not belong to the anatomically shaped isthmus or functional isthmus of the heart can be securely prevented from an ablation. A shape of an ablation element ablating tissue selectively along an isthmus may be a curved line lying approximately within a two-dimensional plane.

Particularly, the term "isthmus" covers any narrow muscular structure (or tract or fiber) defined by two anatomical obstacles such as a vascular orifice of the heart or a valvular structure of the heart. Examples for such isthmus structures are the cavotricuspid isthmus, the area between two pulmonary vein orifices, muscular fibers within or adjacent to the coronary sinus, or other activation pulse/electrically conductive structures within the heart such as Bachmann's bundle or the crista terminalis. An isthmus may be a spatially narrow portion or a bridge or web element which connects two broader electrically conductive structures of heart muscle tissue.

The term "wound filament structure" may particularly denote a structure formed on the basis of one or more filaments (which may be a wire made of a metallic material or a filament made of a non-metallic material such as Dacron, which is a polyester fiber, particularly a condensation polymer obtained from ethylene glycol and terephthalic acid) which is wound for instance to form some kind of helix. One wound helix may form a coiling, whereas several interweaved helices may form a braiding or a mesh.

The term "braiding" may particularly denote an interweaving or twinning of two, three or more separate strands in a diagonally overlapping pattern. The strands may be of one or more materials. Braids can be flat or tubular. A braiding, particularly a metal braiding, may be used to provide a high mechanical stability and at the same time a sufficient flexibility.

The term "coiling" may particularly denote a single flat or tubular strand wound to form a helical structure. A coiling, particularly a metal coiling, may be used to provide a high mechanical stability and at the same time a sufficient flexibility.

The term "braided tubing" or "helical tubing" may particularly denote braidings or coilings integrated within a tube.

According to a first exemplary embodiment of the invention, an ablation system for particularly ablating tissue along an isthmus of the heart is provided. An isthmus may be denoted as a narrow activation pulse conducting structure inside the body that connects two larger structures. More particularly, the isthmus may be a portion in the heart, for instance such as the cavotricuspid isthmus, relatively narrow and forming a curved structure which, according to an exemplary embodiment, is blocked for providing a therapy of isthmus-dependent atrial flutter or another arrhythmia. For that purpose, an ablation catheter of the ablation device may be specifically shaped, sized and dimensioned to follow the anatomical structure of an isthmus of the heart so that the application of an ablation medium after properly positioning the ablation catheter at the isthmus of the heart, may allow for a selective deactivation of an undesired conduction path with low effort and high precision. In a more general sense an isthmus can be any narrow activation pulse conducting connection. For instance muscular bridges within or adjacent to the coronary sinus may form an isthmus of conduction in patients with atypical left atrial flutter.

According to a second exemplary aspect of the invention, an ablation device is provided which may particularly be applied for the ablation of the isthmus of the heart, but also to other anatomical regions. Such an ablation element may comprise a tubular body having a mantle surrounding a braiding and which does not have a uniform thermal equilibration characteristics along a circumference thereof. In contrast to this, such an ablation element may have a varying thermal conductivity along the circumference so that specific portions along the circumference may display a rapid ice formation upon freezing due to a proper thermal conductivity between ablation element and such portions (for instance for ablating a corresponding adjacent tissue material). However, other anatomical portions surrounding the circumference of the thermal body will be influenced only in a negligibly fashion by the thermal properties in an interior of the tubular body. By taking this measure, it is possible to improve the spatial selectivity of the ablation procedure and to ensure that tissue which shall not be influenced by an ablation procedure is in fact not harmed by the ablation. Thus, a spatially well-defined ablation of specific anatomical portions such as in isthmus is possible while at the same time protecting other tissue portions against undesired ablation. Such a configuration may be realized by a circumferentially oval design of the mantle (which may have, for instance, a varying thickness and/or material composition along the circumference) in combination with a mechanically stabilizing braiding core which simultaneously provides for a proper flexibility. Thus, such an ablation element may have both proper mechanical properties for insertion and maintenance within a physiological object as well a proper thermal conductivity properties for precise, efficient and spatially restricted ablation.

Next, further exemplary embodiments of the ablation device according to the first exemplary aspect will be explained. However, these embodiments also apply to the method according to the first exemplary aspect, to the ablation element according to the second exemplary aspect, and to the ablation device according to the second exemplary aspect.

According to an exemplary embodiment of the invention, the ablation device is provided with a handle, the handle comprising a positioning control handle part adapted to be coupled to a positioning catheter of the ablation device and adapted to position the positioning catheter in an object (such as a heart of a human), and an ablation control handle part adapted to be coupled to an ablation catheter of the ablation device and adapted to ablate material of the object (such as an isthmus of a heart of a human) using the ablation catheter. The positioning control handle part and the ablation control handle part may be adapted to be separable (for instance spatially, mechanically and/or functionally) from one another. The term "adapted to be separated from one another" may particularly denote that the positioning control handle part and the ablation control handle part may be functionally and/or spatially separable, for instance made of two different individual components which are not integrally formed and can be selectively connected to one another or disconnected from one another. This includes the opportunity to reversibly eliminate a coupling between the handle parts or to rigidly couple them to one another which may be realized by adjusting the shapes of the connection position or coupling position of the two handle parts accordingly. It may also include that a spatial arrangement of the positioning control handle part and the ablation control handle part relative to one another is alterable to selectively arrange the positioning control handle part and the ablation control handle part at a distance from one another or close to one another. There may or may not be an intermediate piece between the positioning control handle part and the ablation control handle part. Thus, the positioning control handle part and the ablation control handle part may be coupled directly or indirectly.

The positioning control handle part and the ablation control handle part may be adapted to be operable in a first configuration in which the control handle part and the ablation control handle part may be fixedly connected to one another and may be adapted to be operable in a second configuration in which at least one of the control handle part and the ablation control handle part is operable independently from the other one of the control handle part and the ablation control handle part. Thus, due to the specific adaptation of the two handle parts, a first function may be realized in a combined mode and a second function may be realized in a separated mode. For example, for positioning the catheters within a human body, it may be appropriate to fixedly connect the two handle parts to one another for insertion of a tip of the position catheter at a specific location in the human body, for instance at a physiological or anatomical reference or target position. Upon proper positioning of the catheters, the two handle parts may be separated from one another mechanically and may be moved relative to one another for example to trigger a geometrical shape change of the ablation catheter (for instance from a straight linear configuration to a curved configuration). With such a procedure, the ablation line of the ablation catheter may be positioned exactly at a desired anatomical position (such as an isthmus of a heart of a human) which may require for instance folding of this ablation portion which can be triggered by a relative motion of the ablation handle with respect to the position handle. However, it is also possible that, with respect to the previously described configuration, the ablation control handle part and the positioning control handle part change function and/or position so that positioning is performed with the use of only the positioning control handle part, and preparation of the ablation is performed by a combination of both handle parts. In a further configuration, the positioning control handle part is operated alone for positioning, and the ablation control handle part is operated alone for preparing the ablation.

The positioning control handle part and the ablation control handle part may be adapted so that in the first configuration the positioning catheter is positionable at a defined position of the heart and may be adapted so that in the second configuration a shape of the ablation catheter is adjustable to bring it into contact with the material of the isthmus of the heart to be ablated.

The positioning control handle part and the ablation control handle part may be adapted to be fixedly connectable to one another in a detachable manner. The term "fixedly connectable" may denote that, in a mounted or assembled state, the positioning control handle part and the ablation control handle part essentially form a common handle with rigidly connected components, i.e. a single piece. The "detachable" property may denote that the connection is configured such that, with an easy operation, for instance with one hand movement or maneuver, the two handle parts may be separated from one another. This may allow for an easy construction and a simple operation.

The positioning control handle part and the ablation control handle part may be adapted to be connectable to one another by one of the group consisting of a plug-in connection, a bayonet fitting, a magnetic fitting, a snap-in connection, a screw closure and a form closure. Therefore, positive locking mechanisms and non-positive locking mechanisms may be used to connect the two handle parts in a reversible manner.

The positioning control handle part and the ablation control handle part may comprise a common lumen. For example, both of the positioning control handle part and the ablation control handle part may be formed as hollow cylindrical tubes having a connection portion at which the two handle parts may be assembled (directly or indirectly via an intermediate piece) to form a common lumen. Through this common lumen, a plurality of components may be guided for both positioning and ablation preparation as well as for performing the ablation. For example, a positioning or guiding wire for the positioning control may be provided within the lumen. Also the provision of contrast agents or flushing solutions may be performed via a supply conduit guided through the common lumen. Regarding the ablation preparation, a mechanical mechanism for converting the ablation catheter from a retracted operation mode into an expanded operation mode may be guided through the common lumen, for instance a taut wire or a push mechanism. The common lumen may also accommodate electrical connections or an ablation medium supply line such as a cooling agent supply line through which a cooling agent such as nitrous oxide ($N_2O$) can be guided from a container towards the ablation element for ablating the material by shock cooling. Such a refrigerant or coolant may be a compound used in a cooling procedure or cycle that undergoes a phase change from liquid to gas, and optionally back. Such a cooling loop may comprise a tubular line having a lumen through which the refrigerant may be transported, for instance may be pumped. A hollow wall of the cooling loop may be made of a material which properly thermally isolates the refrigerant during circulation along the cooling loop. As an alternative to nitrous oxide, it is also possible to use other cooling agents, for instance liquid nitrogen, liquid helium, liquid oxygen, liquid air, argon, or the like.

An ablation source interface may be provided at the handle and may be adapted for being connected to an ablation source. Such an ablation source may be a container storing a cooling agent such as $N_2O$ or may be an electrical current source for applying a heating current to the ablation catheter. The ablation source interface may be adapted for coupling or connecting to such an ablation source. The positioning control handle part may be arranged between the ablation source interface and the ablation control handle part. Thus, the propagation path of an ablation agent may be from the ablation source through the ablation source interface through the positioning control handle part subsequently through the ablation control handle part and from there into the ablation catheter for application to the surrounding tissue. In such a configuration, an ablation source line may be guided through the positioning control handle part.

An ablation source guide (such as a cooling fluid conduit or an insulated electric wire) may be provided and adapted for being connected to the ablation source via the ablation source interface and may be adapted for guiding an ablation medium (such as a cooling fluid or an electric current) from the ablation source through the positioning control handle part and the ablation control handle part towards the ablation catheter couplable to the ablation control handle part.

The ablation control handle part may be arranged at a distal position of the positioning control handle part. Thus, the ablation control handle part may be arranged between the positioning control handle part on the one hand and the positioning catheter and the ablation catheter (and thus the object in which these catheters are to be inserted) on the other hand. In other words, the ablation control handle part may be arranged closer to the ablation catheter and to the positioning catheter than the position control handle part, and therefore, in a normal operation mode, closer to the patient than the positioning control handle part. This may allow to first operate both handle parts together for a positioning procedure, and to move subsequently the ablation control handle part relative to the positioning control handle part for changing the shape of the ablation element, for instance from an essentially linear to an essentially bent configuration.

To support the turning or rotating motion for such a geometry change, specific functional measures may be taken at the handle. For example, the handle may comprise curved (for instance helical) guide elements (for instance at a connection between the positioning control handle part and the ablation control handle part, or provided at least partially in an intermediate piece sandwiched between the positioning control handle part and the ablation control handle part) to thereby allow to turn/rotate the ablation control handle part relative to the positioning control handle part to promote a shape change of the ablation catheter couplable to the ablation control handle part. Therefore, by moving the two separate handle parts relative to one another, the folding motion of the ablation element may be supported or promoted.

The ablation device may comprise an intermediate piece connected between the positioning control handle part and the ablation control handle part and configured to space the positioning control handle part with regard to the ablation control handle part in a first operation mode, and configured to be received in the positioning control handle part and/or in the ablation control handle part in a second operation mode in which the positioning control handle part abuts against the ablation control handle part.

The positioning catheter may comprise an anchoring mechanism, particularly an inflatable balloon or a biased spring (such as a helical coil), or an extendable or an expandable screw coil (see FIG. 2), adapted for anchoring the positioning catheter at a defined position in the object. For example at a tip of the positioning catheter inserted into the human being, such an anchoring mechanism may be provided which can be operated in a passive mode in which it has a small dimension for insertion, and which can be brought to an active mode in which it has a larger dimension for anchoring. For example, when the tip of the positioning catheter is provided at a target position in the object, the anchoring mechanism may be activated, for instance an inflatable balloon may be inflated or an extendable coil may be screwed into the endocardium (for example an active fixation mechanism similar to a screw in lead used with cardiac pacemakers) or a compressed helical coil may be expanded or an expandable screw coil may be expanded, so that the tip of the positioning catheter is fixed within the object (for instance is fixed in an endocardium of the heart). Such an actuation of the anchoring mechanism may be triggered by a physician using the handle, particularly using the positioning control part, for example by operating a button or turning knob arranged there.

Moreover, the positioning catheter may comprise a guiding shaft for guiding the positioning catheter to a defined position in the object (for example to fix a tip of the positioning catheter in an endocardium while providing for a proper mechanical and thermal contact between an ablation element of the ablation catheter and an isthmus under treatment). Such a guiding shaft may be flexible and at the same time may have some mechanical stability or rigidity so that the guiding shaft can be guided through the tissue of the object to a specific position, thereby flexibly following the anatomical conditions and at the same time providing mechanical stability for proper positioning and insertion.

The positioning catheter may comprise a supply line for supplying the object (for instance a heart) with a supply medium. For instance, it may be necessary or desirable to insert a contrast agent into a specific organ or tissue being so as to perform a contrast agent based measurement to ensure proper positioning of the system. Additionally or alternatively, it may be desired to insert a flushing fluid to the object (for instance a heart), for instance a sodium chloride solution.

The ablation catheter may also comprise an ablation element adapted for ablating a defined portion of the object (for instance an isthmus of the heart) upon supply of an ablation medium to the ablation element by an ablation source. Such an ablation element may or may not comprise electrodes to which an electric current can be applied for heating the tissue to destroy it. Alternatively, the ablation element may comprise a cooling portion of a cooling catheter which can be cooled by an essentially isenthalpic expansion of a cooling agent such as nitrous oxide ($N_2O$). Alternatively, the ablation element can also be an ultrasound emitter for emitting intense ultrasound to a desired position of the object (for instance an isthmus of the heart), to selectively destroy tissue in a spatially selective manner.

The ablation medium may comprise a cooling medium (for example a cooling fluid such as $N_2O$, liquid nitrogen, liquid helium, etc.), a heating medium (for instance an ohmic heating element which can be heated by guiding electric current through it), a high-frequency alternating current (an oscillating current which may also heat by ohmic dissipation), an icing medium (which may cause icing of the desired tissue), ultrasound (which may also provide a high amount of energy at a specific portion of the tissue for destroying the tissue), electromagnetic radiation (for example light, UV, infrared, X-rays, microwaves, etc.), laser radiation (requiring a laser source for providing laser radiation), microwaves, etc. Thus, any ablation medium may be supplied to a specific portion of the tissue (for instance an isthmus of the heart) to destroy it.

The ablation element may comprise or may consist of a shape memory material. With a shape memory material, the ablation element may be maintained in a first state and, only when mechanical pressure is applied via the handle, the material goes back to its stored shape, for instance bent shape. It is also possible that a temperature raise initiated by the body temperature upon insertion of the catheter in a physiological body triggers the ablation element to assume its original shape automatically. For instance, the material may take a predefined shape when being inserted into a warm body.

The ablation catheter may comprise a folding mechanism adapted for being actuable via the ablation control handle part to fold the ablation element into a defined folded configuration. For example, the ablation catheter may have an essentially straight configuration for an easy insertion of the catheters into the object. To bring the ablation catheter into an ablation configuration for ablating a specific portion of the tissue within the object (for instance an isthmus of the heart), the folding mechanism may be actuated. The folding mechanism may be a mechanical mechanism which can be activated by exerting a mechanical force (for instance provided by the physician operating the handle) acting on the folding mechanism. For example, such a force may be enhanced by a relative motion between the two handle parts, by another pressing motion or even by a pulling force which can be actuated by moving the two handle parts relative to one another.

The ablation element may be convertible between a straight configuration and a bent configuration by actuating the ablation control handle part. The straight configuration may be appropriate for inserting the system into the object, and the bent configuration may be adjusted in accordance with the specific anatomical conditions around an isthmus of the heart and may define a portion of the tissue (for instance an isthmus of the heart) which will be ablated subsequently.

The folded or bent configuration of the ablation element may follow an anatomical isthmus shape. By taking this measure, atrial flutter may be eliminated by deactivating a line along the isthmus.

The positioning catheter may be arranged to be at least partially guidable through the ablation control handle part. Particularly for positioning, the positioning catheter may move within the ablation control handle part.

The ablation device may comprise a (single or common or shared) sleeve connected to the handle and accommodating a part of the positioning catheter and a part of the ablation catheter. This sleeve may be formed by a multi-lumen tube which hosts the positioning and the ablation catheter. At least a part of the sleeve may be located between the handle and the portions of the ablation catheter/position catheter which are exposed to/in the object (for instance at an isthmus of the heart). Such a common sleeve accommodating both catheter portions may be highly appropriate since it eases the insertion of the components into the body.

The sleeve may have a first lumen in which the part of the positioning catheter is accommodated. Such a first lumen may have an essentially circular cross-section. Through this circular cross-section the elements related to the positioning catheter may be guided, such as a guide wire, a sodium chloride solution or any other rinse solution, contrast agent, etc. Within the positioning catheter, wires may be guided for conducting electrical signals from electrodes at the distal portion of the positioning catheter to an electrophysiology recording system. A second lumen may be provided in the sleeve in which components of the ablation catheter (for example supply of the ablation medium, thermocouples, etc.) is accommodated. This second lumen may have a kidney shaped cross section (see FIG. 4) or may have an annulus segment shaped cross section (see FIG. 5). In yet another embodiment the second lumen may have a circular cross section. Supply lines and waste lines transporting the ablation medium may be arranged in this kidney or annulus segment or circular shaped cross section. The catheter shaft may be reinforced with a braiding for providing sufficient mechanical stability.

Hence, the first lumen may have a circular cross section and the second lumen may have one of a kidney shaped cross section and an annulus segment shaped cross section.

In addition to the first and the second lumen, it is possible to provide at least one further lumen in the shaft or sleeve, for example to accommodate thermo couples, temperature sensors, etc.

According to an exemplary embodiment, a two-part handle of a cryocatheter may be provided, wherein a first handle portion serves for actuating a positioning catheter, and a second handle part serves for actuating an ablation catheter.

Particularly, a double lumen (or twin lumen) catheter may be provided having a positioning catheter (which may comprise a balloon, a contrast agent supply, measurement electrodes for controlling a correct position). Furthermore, an ablation applicator may be provided (which may carry an element which is actually used for ablation, which may have a shape memory material, a thermoelectric element, and may have a cooling means supply).

For operating such a configuration, the catheters may be inserted into a body in an elongated shape. It is possible that the positioning catheter head is bendable or curvable during insertion. Subsequently, it is possible to anchor a tip of the positioning catheter in a specific portion of a heart by pumping up a balloon or the like. From a backside position of the handle, it is possible to then push or provide a pushing force to thereby trigger bending of the ablation catheter, for instance to form a predefined curved ablation line (which may provide for ablation between a beginning and an end of the line). Then, a specific portion of the tissue may be destroyed by performing an ablation (in accordance with anatomical requirements).

In yet another embodiment the positioning catheter is inserted in the heart via the inferior caval vein and forwarded into the right ventricle via the tricuspid valve. A screwing mechanism is applied for fixing the distal portion of the positioning catheter in the right ventricle. Thus, the positioning catheter now defines a pathway from the right atrium into the right ventricle. Electrodes on the positioning catheter are used for identifying the location of the cavotricuspid isthmus along this pathway. The ablation applicator is then slid along the pathway and located at the isthmus. By delivering one or more ablations the entire line where the ablation applicator crosses the isthmus can be ablated.

In an embodiment the ablation applicator uses cryoablation. Here, when the applicator begins to freeze at the isthmus a positioning of the applicator at the isthmus takes place. By moderate pulling at the twin catheter handle the isthmus is stretched and furrows in its anatomy are smoothed out. This enhances the thermal contact between the applicator and the target tissue and supports the formation of a continuous elongated lesion.

In yet another embodiment the positioning catheter is inserted in the heart via the inferior caval vein and forwarded into the coronary sinus. The ostium of the coronary sinus is located in the posterior septal region of right atrium. The coronary sinus vessel forms a path along the posterior atrioventricular groove to left lateral left atrium. A fixing mechanism (for example a balloon) is applied for fixing the positioning catheter in the distal coronary sinus. In patients with atypical left atrial flutter muscle sleeves within or adjacent to the coronary sinus may form a functional isthmus of conduction within a flutter re-entrant circuit in the left atrium. The signals recorded by electrodes on the positioning catheter may be analyzed for positioning of the slide able ablation applicator along the axis defined by the positioning catheter such that the functional isthmus of conduction can be ablated.

The positioning of the ablation applicator in the examples above may be guided also by various signal parameters such as amplitude, timing (early versus late activation), morphology (for instance fractionated potentials), location (for instance atrial versus ventricular signals) or spectral analysis (for instance dominant frequency).

According to an exemplary embodiment, the shafts or sleeves of the ablation catheter and of the positioning catheter may be provided in common. This feature may be combined advantageously with a two-part handle allowing for a separate operation of the ablation catheter and the positioning catheter.

Using a common shaft may have the advantage that it is possible to omit a taut wire (which however, in other embodiments, can be provided). The ablation catheter may be folded by pushing it from a backward position.

By providing two handles, one handle may be provided which is coupled or connected to the positioning catheter for shifting or sliding or moving the positioning catheter. Another handle portion may be connected to the ablation catheter, to initiate folding and for triggering the ablation procedure.

For inserting the apparatus into a patient, both handle portions may be connected and may be operated in common. For winding the ablation element to a curved line, the two handle portions may be disconnected (so that with one hand, the positioning handle is held, and with the other hand the cryohandle is held). Then, the cryohandle may be translated/slid or rotated with regard to the positioning handle.

The ablation device may comprise a turning knob integrated in the handle for fixing and loosening the fixation mechanism, particularly the screw coil, in the heart.

The tubular body of the ablation element may have a spatially varying wall thickness along the circumference of the tubular body. By varying the wall thickness along the circumference or perimeter of the tubular body, portions of the surrounding medium will abut against a thick part of the tubular body, wherein other portions abut against a thin portion. By adjusting the thermal conductivity of the mantle by the circumferential thickness variation, an easy manufacture of the ablation element is possible. In other words, the material of the mantle along the circumference may be identical according such an embodiment, whereas the spatially varying thermal conductivity properties may be adjusted via the thickness distribution of the mantle. In other words, in such an embodiment, the thickness may be a function of the azimuth angle of the tubular body.

Additionally or alternatively, the tubular body may have a spatially varying material composition along the circumference of the tubular body. In this context, the term "material composition" may denote that the mantle may be formed of one or more different materials, wherein each circumference portion may have one or more material contributions. Therefore, along a circumference of the tubular body, the kind and/or relative proportions of materials may be varied so as to adjust a spatial dependency of the thermal conductivity. For instance, it is possible to provide a constant or varying thickness along the circumference, and a material modification along the perimeter may promote or realize the spatial dependency of the thermal conductivity. For example, combinations or contributions of a good heat conductor and a poor heat conductor may be varied or modulated along the circumference.

The tubular body may have a first circumferential portion having a minimum value of thermal conductivity along the circumference of the tubular body and may have a second circumferential portion having a maximum value of thermal conductivity along the circumference of the tubular body, wherein the first portion and the second portion may be arranged to oppose one another along the circumference. In the context of a tubular body having an essentially circular cross-section, an angle between the first and the second portion may be around 180°. The properly thermally conductivity portion may be positioned close to the organ or tissue to be ablated, whereas the other portion may be aligned towards other tissue material which shall not be ablated and which is therefore securely protected against a strong impact by the ablation procedure.

The spatial dependency of the thermal conductivity along the circumference of the tubular body may be axially symmetric with regard to an axis formed by a center of the first portion and a center of the second portion. By virtually connecting the center of this first portion with the center of the second portion, a line is obtained (or in a three-dimensional image: a plane is obtained), wherein the distribution of the thermal conductivity of the tubular body may be mirror symmetric (with regard to this axis or plane).

The tubular body may be configured to have a gradually varying value of thermal conductivity along the circumference of the tubular body. By gradually varying the thermal conductivity, steps or discontinuities of the physical properties may be avoided. Hence, the value of thermal conductivity along the circumference of the tubular body may vary continuously differentiable.

In an embodiment in which the ablation element is integrally formed of a single material, the tubular body may comprise polyurethane (PUR) or any other thermally conductivity plastic material. By simply varying a thickness of the PUR material along the circumference, an ablation element made of a single material may be obtained in which the thickness determines the degree of thermal coupling between an ablation medium such as a cooling medium such as $N_2O$ and an outer environment.

Alternatively, the tubular body may comprise a core formed by a (for instance metal) braiding and comprises a mantle (for instance formed by a plastic material) surrounding the core. The (for instance metal) braiding may have the effect of mechanically stabilizing the ablation element (for instance to provide for a sufficient pressure resistance or compression strength), but may also contribute to an antikink function. Examples for an appropriate material for the core are copper, iron, aluminum, or steel.

The mantle (which may be formed by the plastic material) surrounding the core may have a varying thickness along the circumference. This thickness may be zero (or close to but different from zero) at a specific angular position, and may significantly differ from zero at another specific portion along the circumference. The combination of a metal braiding and a plastic mantle having a varying thickness has turned out to be an extremely efficient embodiment of the ablation element.

For example, the mantle may comprise polyamide or any other poorly thermally conductive plastic material. At angular positions of the ablation element at which the thickness is small, a proper thermal conductivity between an interior and exterior of the tubular body is achieved. In contrast to this, in portions where the thickness is larger, the thermal coupling can be selectively weakened.

The tubular body may optionally comprise a (for instance tubular) liner lining an inner surface of the core. Such a liner may be a plastic liner protecting an interior of the inner surface of the metal braiding. Such a liner may have a constant thickness over the circumference, or may also have a varying thickness along the circumference, thereby contributing to the spatial dependency of the thermal conductivity along the perimeter.

The (for instance metal) braiding may comprise a shape memory material in which a predefined shape may be stored. In other words, the metal braiding may have stored therein a specific shape which can be recovered (for instance by a thermal triggering or mechanic triggering, so that a desired shape of the ablation element (for instance adjusted to the anatomic geometry of an isthmus of the heart) may be prestored in the system.

An ablation medium such as a cooling fluid or a heating electric current may be supplied to the lumen of the tubular body during an ablation procedure, thereby allowing to thermally couple this thermal energy to a specific portion of the tissue to be ablated.

In the following, further aspects are disclosed:

Aspect 1: An ablation element for an ablation device, the ablation element comprising a tubular body defining an inner lumen;

wherein the tubular body comprises a core formed by a wound filament structure and comprises a mantle surrounding the core;

wherein the tubular body, particularly the mantle, is configured to have a spatially varying value of thermal conductivity along a circumference of the tubular body.

Aspect 2: The ablation element according to aspect 1, wherein the tubular body, particularly the mantle, has a spatially varying wall thickness along the circumference of the tubular body.

Aspect 3: The ablation element according to aspect 1 or 2, wherein the tubular body has a spatially varying material composition along the circumference of the tubular body.

Aspect 4: The ablation element according to aspect 1 or any one of the above aspects, wherein the tubular body has a first portion having a minimum value of thermal conductivity along the circumference of the tubular body and has a second portion having a maximum value of thermal conductivity along the circumference of the tubular body, wherein the first portion and the second portion are arranged to oppose one another along the circumference.

Aspect 5: The ablation element according to aspect 4, wherein the spatial dependence of the thermal conductivity along the circumference of the tubular body is axially symmetric with regard to a mirror axis formed by a center of the first portion and by a center of the second portion.

Aspect 6: The ablation element according to aspect 1 or any one of the above aspects, wherein the tubular body is configured to have a gradually varying, particularly a continuously differentiable, value of thermal conductivity along the circumference of the tubular body Aspect 7: The ablation element according to aspect 1 or any one of the above aspects, wherein the wound filament structure is formed by a braiding or by a coiling.

Aspect 8: The ablation element according to aspect 1 or any one of the above aspects, wherein the wound filament structure is formed by a metal braiding or a metal coiling and the mantle is formed by a plastic material surrounding the core.

Aspect 9: The ablation element according to aspect 1 or any one of the above aspects, wherein the mantle comprises polyamide.

Aspect 10: The ablation element according to aspect 1 or any one of the above aspects, wherein the tubular body comprises a liner lining an inner surface of the core.

Aspect 11: The ablation element according to aspect 1 or any one of the above aspects, wherein the braiding or coiling comprises a shape memory material in which a predefined shape is stored.

Aspect 12: An ablation device, the ablation device comprising an ablation element according to aspect 1 or any one of the above aspects adapted for ablating a defined portion of an object upon supply of an ablation medium to the ablation element by an ablation source.

Aspect 13: The ablation device according to aspect 12, comprising at least one of the features of the ablation device according to aspect 1 or any one of the above aspects.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

FIG. 6 illustrates a handle according to an exemplary embodiment in a first operation mode.

The illustration in the drawing is schematically. In different drawings, similar or identical elements are provided with the same reference signs.

Figure 1:
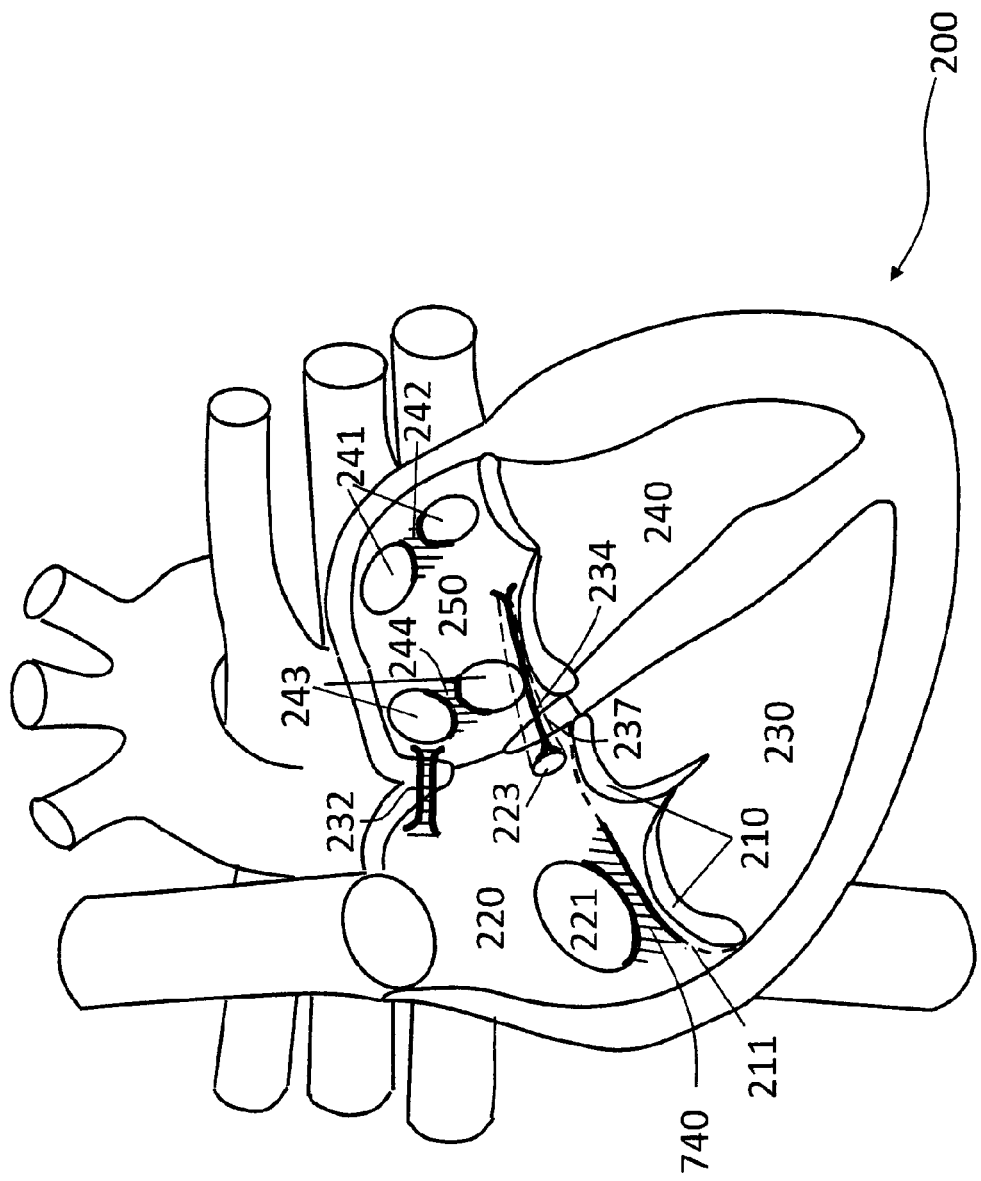
FIG. 1 shows some examples for isthmus structures in the heart.

FIG. 1 shows some examples for isthmus structures in the heart. A four chamber view of the heart 200 is shown with cross sections of the right atrial chamber 220, the left atrial chamber 250, the right ventricular chamber 230 and the left ventricular chamber 240. The flaps of the tricuspid valve 210 are located between the right atrium 220 and the right ventricle 230. The tricuspid rim 211 defines the basal border of electrically conducting muscle tissue of the right atrium. Between the ostium of the inferior caval vein 221 and the tricuspid rim 211 the cavotricuspid isthmus 740 (hatched area) as a narrow muscular bridge connects two larger patches of right atrial muscle tissue. In the left atrium a narrow muscular bridge between the two left pulmonary vein ostia 241 defines an isthmus structure 242. Similarly, between the two right pulmonary vein ostia 243, an isthmus structure 244 is present. Furthermore the Bachmanns bundle 232 (a muscular bundle connecting the anterior right and left atrium) defines an isthmus of conduction. The coronary sinus 237 is a vein at the posterior base of the heart. Here muscle fibers 234 connect the muscular tissue around the ostium 223 of the coronary sinus with the left atrial muscular tissue defining an extremely narrow isthmus of conduction.

If an isthmus structure is a part of the pathway of a re-entry tachycardia, the ablation of the isthmus is an interesting therapeutic option as the re-entry path can be blocked in a narrow segment. This reduces the amount of tissue which has to be destroyed during catheter ablation.

Figure 2:
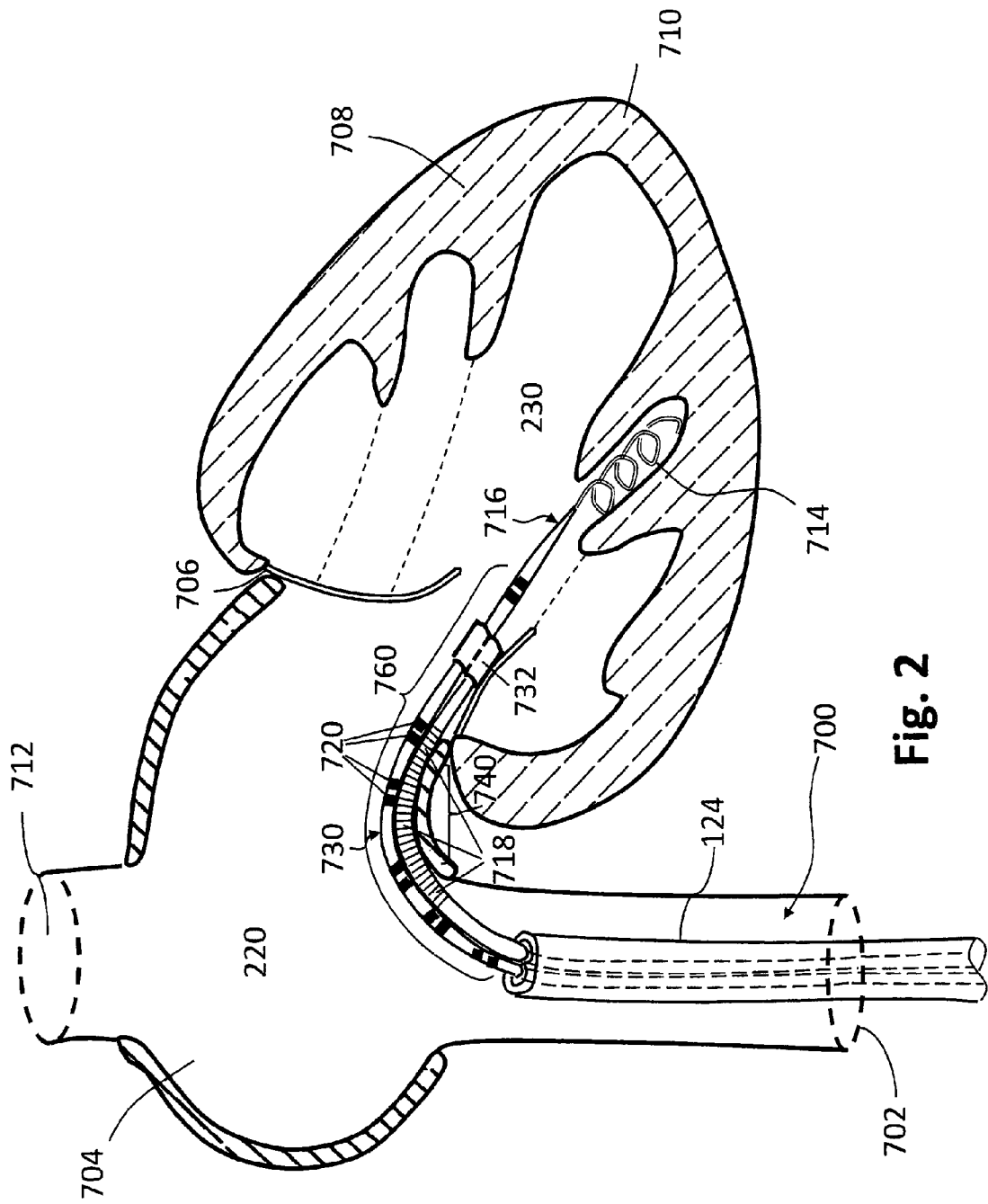
FIG. 2 shows an ablation device according to an exemplary embodiment inserted into a human heart to treat the cavotricuspid isthmus.

FIG. 2 shows an ablation device 700 according to an exemplary embodiment of the invention which is inserted into a human heart.

The inferior vena cava is denoted with reference numeral 702. The right atrium is denoted with reference numeral 704. The tricuspid annulus is denoted with reference numeral 706. Reference numeral 708 shows the right ventricular muscle. Reference numeral 710 shows the apex, reference numeral 712 shows the superior vena cava.

A screw coil 714 is provided at an end of the ablation device. 700 so that the expandable screw coil 714 can serve as an anchoring mechanism for fixing a tip of a positioning catheter 716 in a specific portion of the heart, namely in the endocardium (see FIG. 2). An ablation applicator or ablation element 718 is positioned in such a manner that isthmus tissue 740 can be selectively deactivated by cooling the ablation applicator 718. Ring electrodes 720 are provided for performing a measurement of the position of the positioning catheter 716 relative to the cavotricuspid isthmus 740, so that the correct positioning of the ablation device 700 in the heart can be ensured. After a proper positioning of the positioning catheter 716 and an ablation catheter 730 guided through a common sleeve 124 of the positioning catheter 716 and the ablation catheter 730, the ablation procedure may be started by supplying a refrigerant through the ablation applicator 718.

According to the embodiment of FIG. 2, the ablation catheter 730 may be provided for the interventional therapy of isthmus dependent atrial flutter. The cavotricuspid isthmus 740 is a small muscle bridge between the intersection of the inferior vena cava 702 and the tricuspid annulus 706. In patients having an isthmus dependent atrial flutter, the isthmus 740 has a conductivity for an electrical activation pulse and therefore forms the substrate of the arrhythmia. An interruption of this line by an ablation is supposed to terminate the arrhythmia.

The ablation device 700 shown in FIG. 2 has a double catheter design (twin catheter). The two catheter portions are the positioning catheter 716 and the ablation catheter 730. The positioning catheter 716 comprises at its distal end the anchoring screw coil 714. By suitable control mechanisms, the positioning catheter 716 is advanced into the right ventricular chamber 230, more particularly may be fixed in an endocardium. For this purpose, a taut wire, a sheath, a guiding wire, etc. may be used. By means of the anchorable screw coil 714, the positioning catheter 716 is anchored at its tip in the right ventricular muscle 708.

Proximal from the screw coil 714, the ring electrodes 720 are arranged along a certain extension (catheter neck 760). In an embodiment, the ring electrodes 720 are arranged in a pairwise manner so that bipolar electrograms can be measured. By a moderate pull at the proximal catheter end (handle, not shown in FIG. 2), a portion of the catheter neck 760 abuts against the isthmus 740. By an evaluation of the electrograms it can be determined in which position the catheter device 700 is abutting at the isthmus (ablation target) 740.

The ablation catheter 730 can be guided via sleeves 732 at the positioning catheter 716. At the distal end, the ablation applicator 718 is provided which can be slid in a forward or backward direction (see sleeve 732). This can be performed using a sliding carriage mechanism.

The ablation applicator 718 can also be positioned under the assistance of imaging methods (for instance X-ray imaging) wherein the electrodes 720 may serve as markers of the isthmus 740. By the distal fixing of the positioning catheter 716, it is now possible by forceful pulling at the twin catheter to smoothly press the isthmus 740 to the contact line of the catheter 730, in order to provide a proper contact.

The carriage of the ablation applicator 718 may be slid in a forward direction and can be positioned via marking electrodes 720 at the isthmus 740.

Again referring to element 714 shown in FIG. 2, such an element may serve as a fixation mechanism for a guide catheter of the cool line catheter 700. Such a screw coil may work in a similar manner as a small corkscrew, wherein the screw coil can be extended by turning a central core at a proximal end of the catheter, to thereby screw the element 714 into the endocardium.

Figure 3:
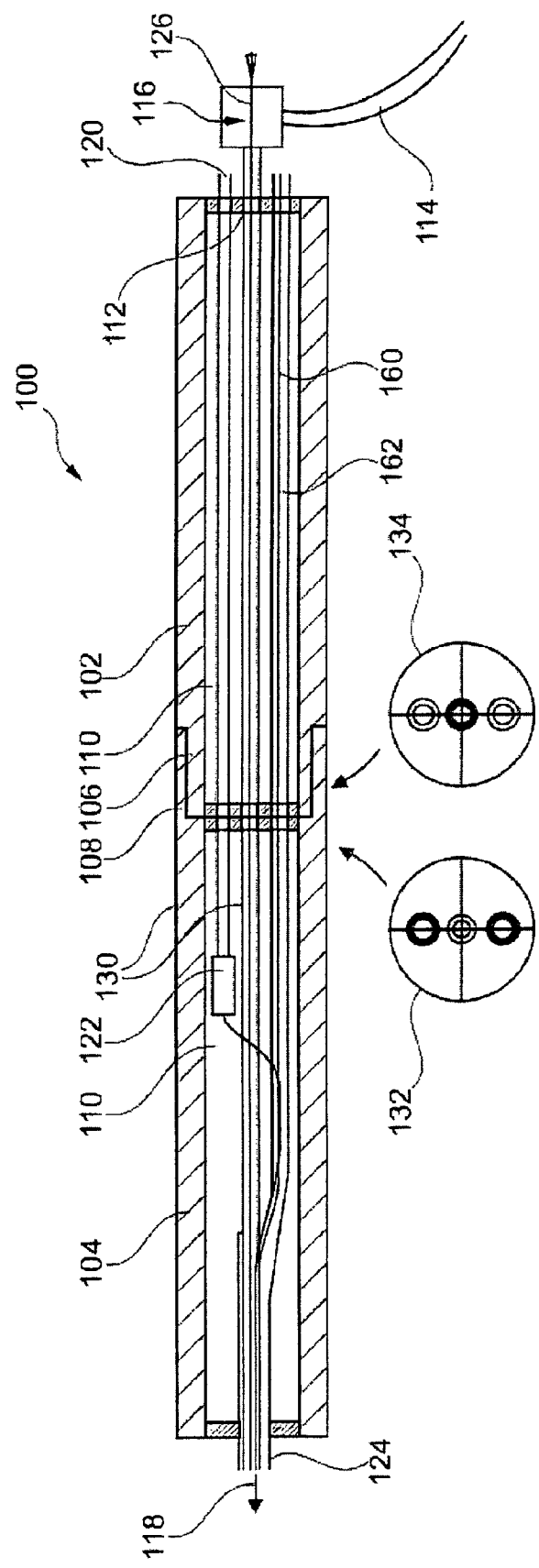
FIG. 3 illustrates a handle according to an exemplary embodiment.

FIG. 3 shows a handle 100 for an ablation device (such as the ablation device 700 shown in FIG. 2) according to an exemplary embodiment of the invention.

The handle 100 comprises a positioning control handle part 102 adapted to be coupled to a positioning catheter of the ablation device and adapted to position the positioning catheter in a patient. Furthermore, the handle 100 comprises an ablation control handle part 104 adapted to be coupled to an ablation catheter of the ablation device and adapted to ablate material of the patient using the ablation catheter. By plugging a male part 106 of the positioning control handle part 102 into a female recess 108 of the ablation control handle part 104, it is possible to selectively connect the positioning control handle part 102 to the ablation control handle part 104 or to separate both control handle parts 102, 104 from one another.

In a connected operation mode of the components 102, 104 (as shown in FIG. 3), the positioning control handle part 102 and the ablation control handle part 104 are rigidly connected to one another. In this operation mode, they can be used to insert a positioning catheter into a human body. In a second operation mode, the positioning control handle part 102 may be separated or disassembled from the ablation control handle part 104 so that the ablation control handle part 104 can be moved alone towards the object (for instance to trigger a bending of the ablation catheter) while the positioning control handle part 102 is maintained essentially spatially fixed.

As can be taken from FIG. 3, the positioning control handle part 102 and the ablation control handle part 104 form a common lumen 110 through which a plurality of items are guided. The cooling medium supply line 160 is connected at the positioning control handle part 102 so as to allow connecting a nitrous oxide source as a cooling agent via a supply line 160 to guide it towards the ablation catheter (see arrow 118). Furthermore, a cable 120 is guided through the lumen 110. The cable 120 is connected to an electronic module 122 (which may be an integrated circuit) which may provide an electronic function.

A common catheter shaft 124 accommodates all components needed for a communication of fluids and electric signals between the handle 100 and the catheters of the cryoablation device.

A guiding wire is denoted with reference numeral 126 and is guided through the lumen 110 towards the catheters. At the interface 106, 108, a plurality of sealing units 130 (such as sealing rings) are provided.

Furthermore, cross sections 132, 134 show the various connections formed around the sealing portion 130.

A bank of taps (not shown) may be provided coupled to the cooling line 160.

The handle 100 may be arranged as a two-part handle 102, 104 for twin catheters. The handle portion 102 is assigned to the positioning catheter, and the other handle portion 104 (ablation handle) is assigned to the ablation catheter. All components related to the ablation catheter (supply of the ablation energy, electronics) are fixedly connected or connected via plug connections. All supply connections related to the positioning catheter (for instance contrast agent, rinse fluid) are connected to the positioning handle 102. The ablation handle 104 is arranged at a distal position from the positioning handle 102 and is detachably connected to it (for instance by a plug connection, a bayonet connection). The positioning catheter is slidable via the ablation handle 104. The connected handles 102, 104 define the passive position for inserting and positioning, and for retracting the catheters. For bringing the catheter into an active position (for ablation), the ablation handle 104 is slid in a direction distally from the positioning handle 102, so that the ablation catheter slides over the positioning catheter.

As an alternative to FIG. 3, the positions of the handles 102, 104 can be exchanged.

A flushing line 114 is connected to the homeostatic valve 116.

A cooling fluid drain (refrigerant backflow) unit for guiding the expanded cooling fluid apart or away from the device 100 is denoted with reference numeral 162.

Figure 4:
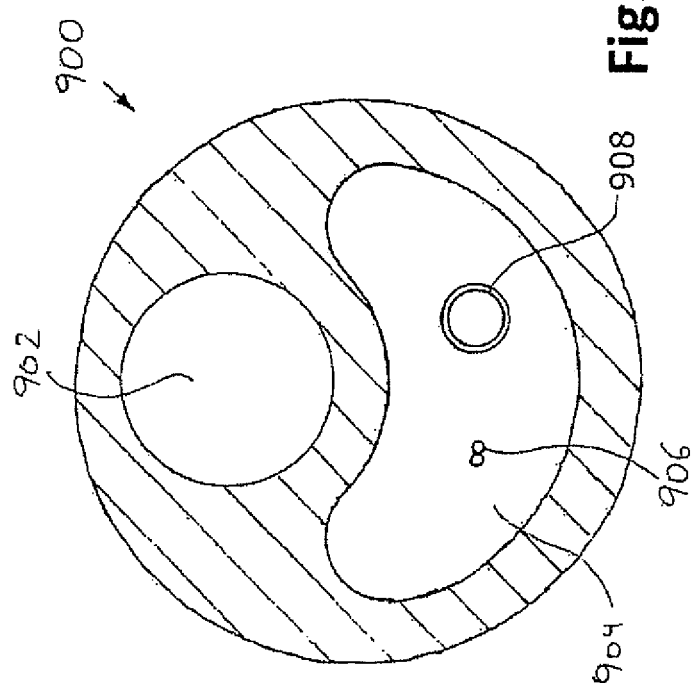

FIG. 4 shows a cross section of a common sleeve 900 (an example for the design of reference numeral 124 in FIG. 2 and FIG. 3) according to an exemplary embodiment.

The common sleeve 900 for receiving components of the positioning catheter and the ablation catheter comprises a circular lumen 902 through which the components for operating the positioning catheter can be guided, for instance a sodium chloride solution. Through a kidney shaped lumen 904, various components for the ablation catheter may be guided such as a thermo element 906 for performing a temperature measurement, a cooling agent supply line 908 and a cooling agent backflow lumen 904. The material of the sleeve 900 may be a plastic material or any other suitable flexible material. Via the supply line 908, a cooling agent (such as $N_2O$) can be conducted to a tip of the ablation catheter, and via the backflow lumen 904, the expanded cooling agent in gaseous form may be transported back to exhaustion.

Figure 5:
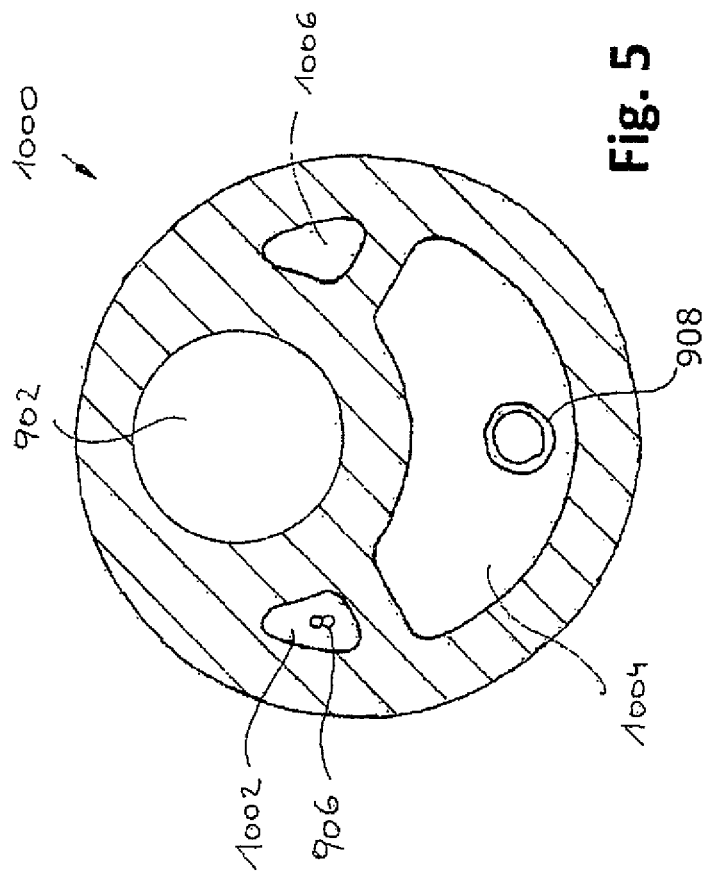
FIG. 4 and FIG. 5 show cross sections of integrally formed sleeves for receiving application catheter and positioning catheter according to an exemplary embodiment.

FIG. 5 shows a common sleeve 1000 (an example for the design of reference numeral 124 in FIG. 2 and FIG. 3) according to another exemplary embodiment of the invention.

In the embodiment of FIG. 5, the thermo couple 906 is provided in a separate lumen 1002 so as to avoid undesired interaction with other components. An annulus segment shaped lumen 1004 is provided which accommodates a cooling agent supply line 908 and forms a cooling agent backflow lumen 1004. At least one further lumen 1006 may be provided to accommodate optional further elements. Also the lumens 1002 and 1006 may be used for guiding the refrigerant backflow. The backflow might be guided using multiple lumen in parallel or by using only one lumen.

Thus, it is possible to implement a sleeve 900, 1000 for use with an oblong shaft of the ablation catheter having two lumen. One lumen having a kidney shaped cross section (see reference numeral 904) and a second lumen 902. The kidney shaped lumen 904 can be used as an inner lumen of the ablation applicator. In this lumen 906, all required lines for supplying the ablation energy may be provided. The other lumen 902 having essentially circular cross section may receive components of the positioning catheter. Within the circular cross section 902, the positioning catheter may be rotated relatively to the ablation catheter.

The material of the sleeve 1000 may be stiff to be mechanically stable, for example the sleeve might have a desired torque stiffness. The bridges between lumen 1002 and 1004 or 1006 and 1004 might prevent the kidney shaped lumen from kinking.

Figure 7:
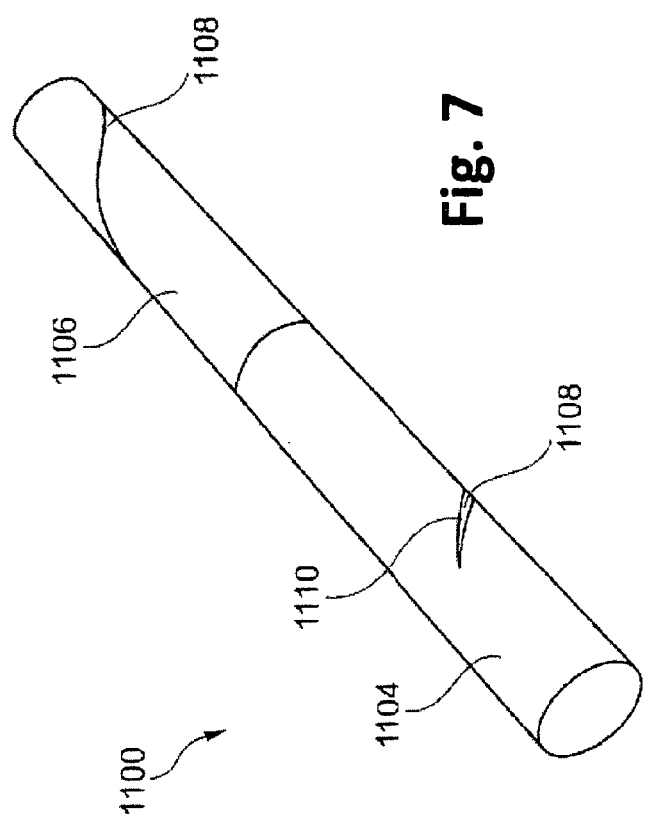
FIG. 7 illustrates the handle of FIG. 6 in a second operation mode.

FIG. 6 and FIG. 7 illustrate a handle 1100 according to an exemplary embodiment in different operation modes.

FIG. 6 shows the handle 1100 in an extended state, whereas FIG. 7 shows the handle 1100 in a retracted state.

The handle 1100 comprises a tubular intermediate piece 1102 connected between a tubular positioning control handle part 1104 and a tubular ablation control handle part 1106. The tubular intermediate piece 1102 has a slightly smaller diameter than the tubular positioning control handle part 1104 and the tubular ablation control handle part 1106. In the operation mode of FIG. 6, the tubular intermediate piece 1102 serves as a spacer for keeping the positioning control handle part 1104 at a distance d from the ablation control handle part 1106. In the operation mode of FIG. 7, the tubular intermediate piece 1102 is received/accommodated within the positioning control handle part 1104 and in the ablation control handle part 1106 so that the positioning control handle part 1104 almost abuts against the ablation control handle part 1106. The tubular intermediate piece 1102 serves to allow to either spatially separate the positioning control handle part 1104 from the ablation control handle part 1106, or to allow to have the positioning control handle part 1104 and the ablation control handle part 1106 close together.

Each of the tubular positioning control handle part 1104 and the tubular ablation control handle part 1106 comprises a guide groove 1108 along which a guide pin 1110 can be guided to convert the handle 1100 between the extended state and the retracted state, by a hand movement.

The configuration, operation and internal construction of the tubular positioning control handle part 1104 and the tubular ablation control handle part 1106 may be similar as described above, for instance referring to FIG. 3.

In the following, some further explanations of exemplary embodiments of the invention will be given.

Using an appropriate energy source for ablation (for instance high frequency alternating current, icing, ultrasound, laser, microwave), a destroyed line can be generated at the contact portion, for instance by cryoablation. It is possible to perform a plurality of ablation procedures to obtain a desired ablation geometry.

Further connections for rinse fluid, contrast agents, etc. are possible.

In the following, referring to FIG. 8, an ablation element 800 according to an exemplary embodiment of the invention will be explained.

Particularly, the ablation element 800 may be configured to be used as the ablation element 718 shown in FIG. 2.

The ablation element 800 for the ablation device 100 comprises a tubular body delimiting an inner lumen 802 against an environment such as heart tissue, when the ablation element 800 is inserted into a human heart. The inner lumen 802 may serve to accommodate specific members such as electronic wires, cool fluid lines, temperature sensors, etc.

Particularly, the tubular body 800 is configured to have a spatially varying value of thermal conductivity along a circumference of the tubular body, as will be described in the following. Along the circumference of the tubular body shown in FIG. 8, the material composition also varies.

Figure 8:
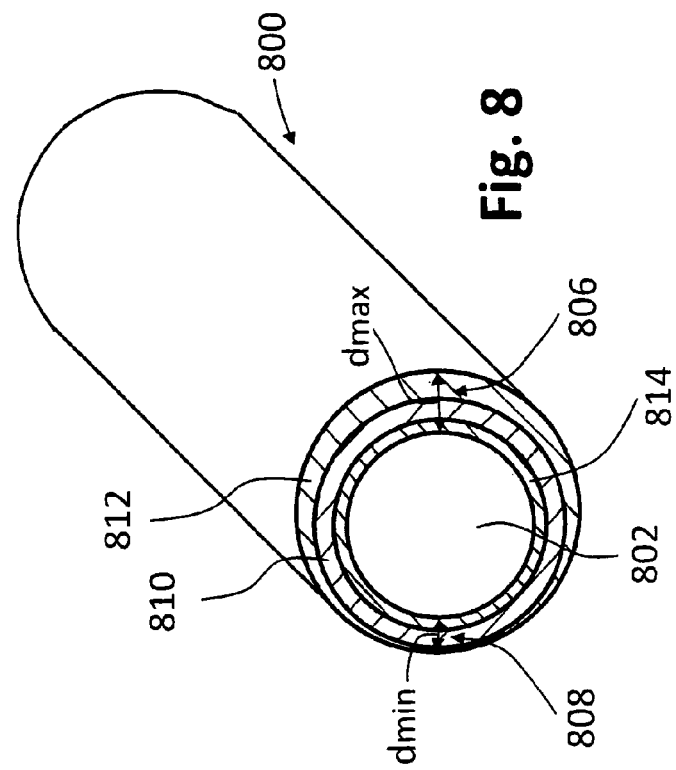
FIG. 8 is a schematic three-dimensional view of an ablation element according to an exemplary embodiment.

In the embodiment of FIG. 8, the tubular body has a spatially varying wall thickness which has values between $d_{min}$ and $d_{max}$, as illustrated in FIG. 8. The tubular body has a first portion 806 close to $d_{max}$ where a minimum value of thermal conductivity or thermal coupling between the lumen 802 and the environment is obtained, and has a second portion 808 close to the region $d_{min}$ where a maximum value of thermal conductivity along the circumference of the tubular body is achieved. As can be taken from FIG. 8, the first portion 806 and the second portion 808 are arranged to oppose one another along the circumference, i.e. have an angular distance of about 180°.

Between the first and the second portion 806, 808 a gradual change of the value of thermal conductivity along the circumference occurs by gradually varying the thickness of the tubular body which gradual change is symmetric in the clockwise and counter clockwise direction connecting $d_{max}$ and $d_{min}$.

More particularly, the tubular body comprises a core 810 formed by a copper braiding and comprises a mantle 812 formed by a poorly thermally conductive plastic material such as polyamide and surrounding the core 810. Moreover, the tubular body comprises a thin lining 814 lining an inner surface of the core 810 and having a constant thickness over the circumference of the tubular body in the embodiment of FIG. 8.

When conducting a cooling fluid through the inner lumen 802, the thermal conductivity in the region $d_{min}$ is a maximum due to the proper conductivity of the metal braiding 810 and the small local thickness of essentially zero of the poorly thermally conductivity mantle 812. Therefore, the ablation will have the strongest impact in the region 808. In contrast to this, the thickness of the poorly thermally conductive mantle 812 is maximum close to the portion 806, so that an abutting tissue portion will remain essentially uninfluenced during the ablation procedure due to the thermally insulating effect of the thick thermally insulating mantle 812 close to the portion 806.

In another application, the portion 806 is irrigated by a warm blood flow. Here the high wall thickness isolates the boiling chamber from the thermal load composed by the blood flow and contributes to an efficient use of the supplied refrigerant.

Figure 10:
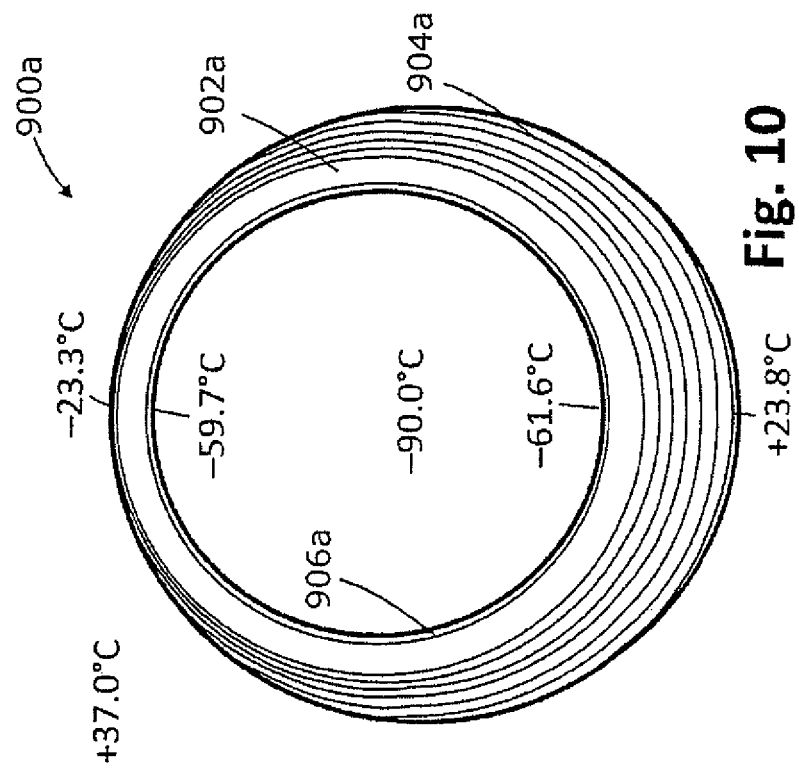
FIG. 10 shows an ablation element according to an exemplary embodiment comprising a copper braiding and a polyamide mantle according to an exemplary embodiment.
Figure 9:
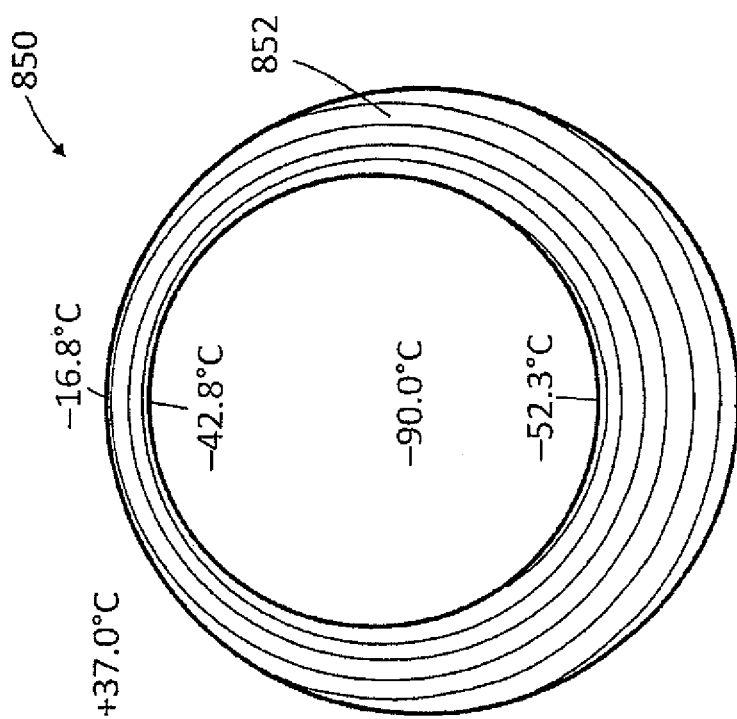
FIG. 9 shows an ablation element consisting of polyurethane.

FIG. 9 and FIG. 10 illustrate the use of different sleeves with a variable wall thickness in order to provide for an increased heat exchange towards the tissue to be ablated (see region 808 in FIG. 8). On the side opposing the tissue (see region 806 in FIG. 8), it is desired to have an essentially thermally insulating property (which can be achieved by a large wall thickness). A finite element computer model has been applied for estimating the temperature field in a warm blood stream (+37° C.). Within the boiling chamber of the catheter a temperature of −90° C. has been assumed. Isotemperature lines are shown at a spacing of 10° C. in both figures.

In the configuration of FIG. 9 showing an ablation element 850, a plastic tube 852 having a high thermal conductivity is used (such as made of polyurethane, PUR), which allows to obtain about −17° at the thin side. On the insulating side, the high thermal conductivity is an undesired effect. The cool power flow here is still more than 50% of the value at the thinnest portion, resulting in a temperature of about 6° C.

The ablation element 850 of FIG. 9 is formed of a single PUR tube 852 having a varying thickness along the circumference of the ablation element 850.

As compared to FIG. 9, the exemplary embodiment of the invention shown in FIG. 10 may be more preferred.

An ablation element 900a shown in FIG. 10 has a metallic braiding element 902a surrounded by a poorly conductive plastic mantle such as a polyamide mantle 904a having a varying thickness along the circumference of the ablation element 900a. Due to the high thermal conductivity of the braiding or coiling only small temperature differences occur in the metal. Isothermal lines have a large distance in the metal. The thickness of the mantle 904a is very small at the properly conductive portion of the ablation element 900a at which the temperature is about −23° C. (where the mantle 904a has a thickness of 0.03 mm). Furthermore, a protection lining 906a in an interior of the metallic braiding 904a is shown which has constant thickness of 0.03 mm over the entire perimeter. However, it is also possible that the element 906a is omitted entirely or selectively in the portion close to the temperature −23° C. to further improve the thermal conductivity. Thus, the thickness of the lining 906a may also vary along the circumference.

As can be taken from FIG. 10, the portion denoted with the temperature 23.8° C. is basically not negatively influenced by the ablation procedure, whereas an efficient ablation is possible in the region close to −23.3° C.

Due to the poor thermal conductivity of the plastic material of the components 904a, 906a, a spatially restricted ablation property is obtained. The heat flow at an outer portion is 25% of the value of the smallest thickness (indicated with −23.3° C.). In an interior portion, the temperature is essentially constant, so that the surface of the boiling chamber for evaporating the cooling medium such as $N_2O$ is ensured in a constant or uniform manner.

The metal braiding 902a improves a mechanical stability of the tube 900a (pressure resistance, anti-kink protection). It is also possible to have larger wall thicknesses than 0.15 mm (as in FIG. 10) for the metallic braiding 902a, which may further improve the mechanical stability. It is possible to use a metallic braiding 902a having a shape memory material.

Figure 11:
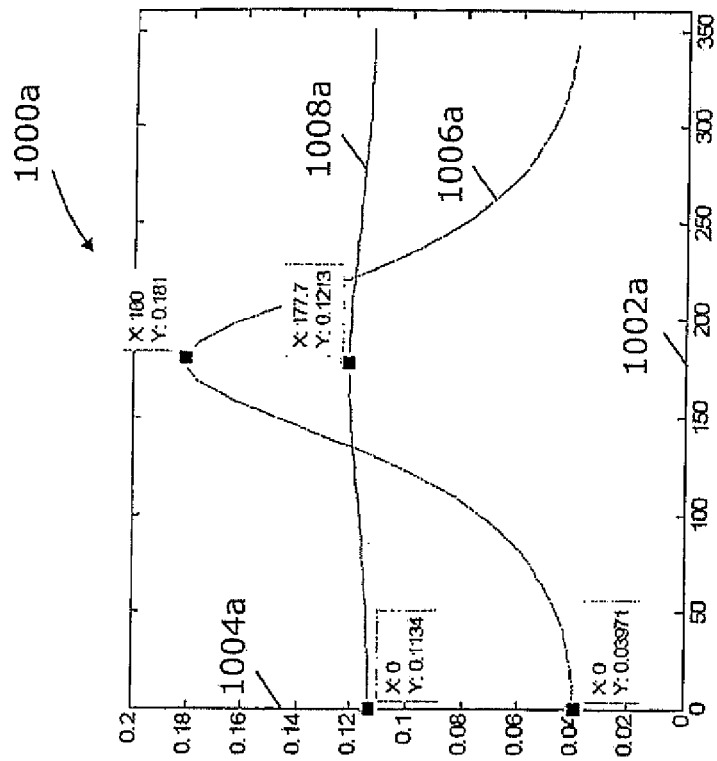
FIG. 11 is a diagram showing the power flow density for the mantle with braiding configuration of FIG. 10.

FIG. 11 is a diagram 1000a illustrating the properties of the ablation element 900.

The diagram 1000a has an abscissa 1002a along which the azimuth is plotted in degree. Along an ordinate 1004a, the power density is plotted in $W/mm^2$.

A first curve 1006a illustrates the power flow density at an outer circumference, whereas the second curve 1008a illustrates the power flow density in an interior position. The power flow at the inner circumference is almost constant. At the outer circumference the heat flow is much higher for the thin area closer to the target tissue. Thus the metal coiling or braiding conducts the heat flow to the tissue.

Figure 12:
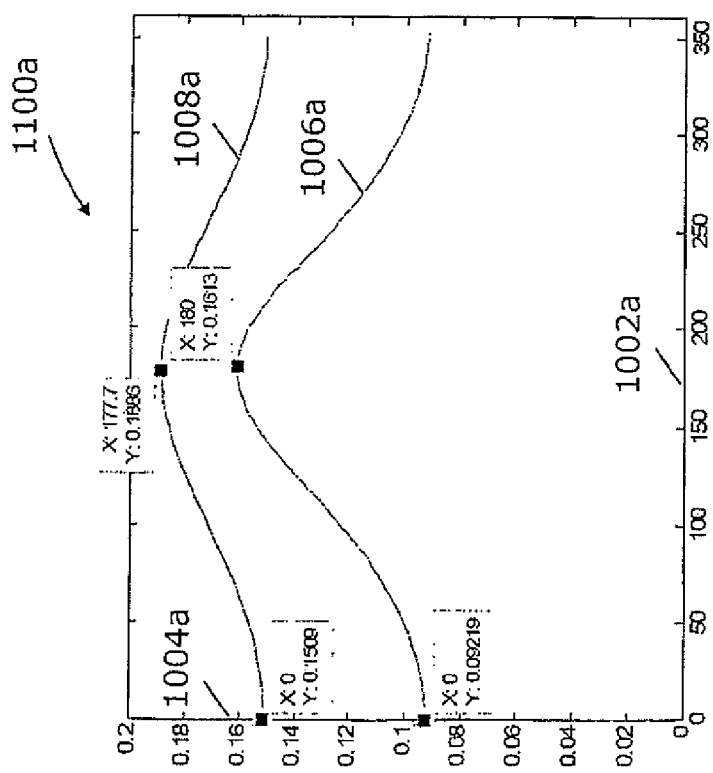
FIG. 12 is a diagram showing the power flow density for an ablation element consisting of polyurethane shown in FIG. 9.

FIG. 12 shows a diagram 1100a showing the dependency of the power density from the angular position for the ablation element 850. Note that here the heat flow at the inner circumference is higher compared to the embodiment in FIG. 11. This means that more refrigerant is needed for maintaining the low temperature in the boiling chamber. In contrast the heat flow in the thin area is smaller. This means that slightly less cooling power can be withdrawn from the target tissue.

Figure 13:
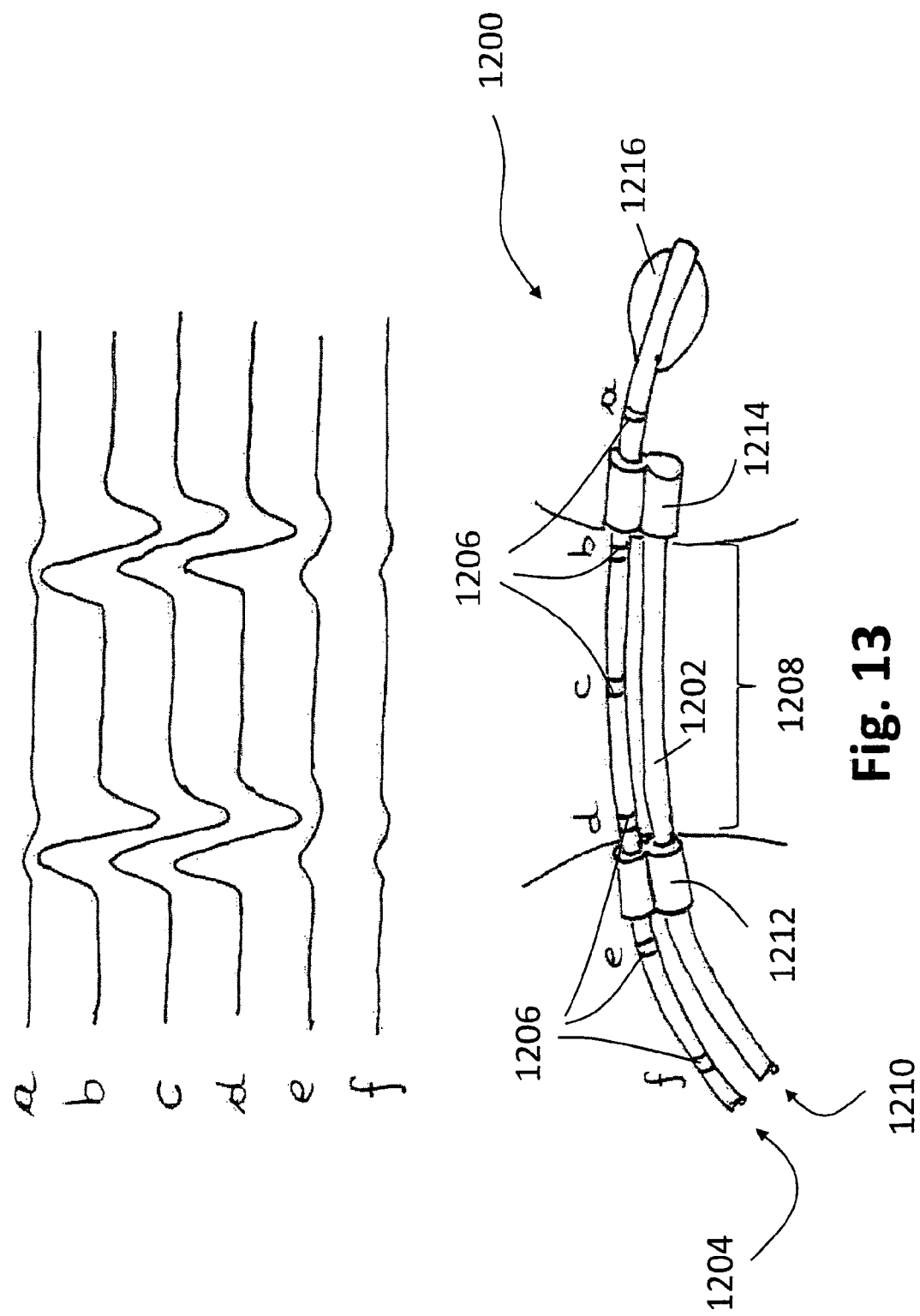
FIG. 13 shows an ablation device according to an exemplary embodiment of the invention.

FIG. 13 exemplarily illustrates how an ablation applicator 1202 of an ablation device 1200 according to an exemplary embodiment of the invention can be positioned.

A positioning catheter 1204 carries multiple bipolar electrode pairs 1206 along its shaft. A subset of the recorded bipolar signals (a, b, c, d, e, f) is depicted in FIG. 13 as well. In this example the bipolar recordings taken at the isthmus 1208 display the highest amplitude. The ablation applicator 1202 is the portion of an ablation catheter 1210 limited by a distal guiding sleeve 1212 and a proximal guiding sleeve 1214. The ablation applicator 1202 is slid along the positioning catheter 1204 until it is next to the electrode pairs 1206 in the isthmus region 1208. This positioning may be confirmed by an imaging approach such as X-ray fluoroscopy. When the ablation applicator 1202 traverses the isthmus 1208, the ablation is started.

If the ablation applicator 1202 is too short for ablating the entire isthmus 1208 by a single ablation cycle multiple ablation cycles may be carried out with proper repositioning of the ablation applicator 1202 after each ablation cycle. The positioning catheter 1204 carries a fixation mechanism such as an inflatable balloon 1216 on its distal end.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. An ablation device, the ablation device comprising:
   a positioning catheter adapted to be positionable in a heart and comprising a fixation mechanism for fixing the positioning catheter in the heart;
   an ablation catheter adapted to ablate material of the heart using the ablation catheter;
   wherein the ablation device is designed to form a continuous elongated lesion and to ablate tissue selectively along an isthmus of the heart;
   wherein the positioning catheter and the ablation catheter are provided to be movable relative to one another;
   wherein the ablation catheter can be guided via sleeves at the positioning catheter;
   wherein the positioning catheter comprises electrodes for recording signals to be analyzed for positioning a slidable ablation element of the ablation catheter along the positioning catheter such that the isthmus can be ablated;
   wherein the electrodes are arranged proximal from the fixation mechanism along an extension of the positioning catheter, wherein a portion of the extension is abutable against the isthmus;
   wherein the ablation element comprises a tubular body defining an inner lumen; and
   wherein the tubular body is configured to have a spatially varying value of thermal conductivity along a circumference of the tubular body.

2. The ablation device according to claim 1, wherein the fixation mechanism comprises an anchoring mechanism adapted for anchoring the positioning catheter at a defined position in the heart.

3. The ablation device according to claim 1, wherein the positioning catheter comprises a guiding shaft for guiding the positioning catheter to a defined position in the heart.

4. The ablation device according to claim 1, wherein the positioning catheter comprises a supply line for supplying the heart with a supply medium, of at least one of the group consisting of a contrast agent and a flushing solution.

5. The ablation device according to claim 1, wherein the ablation element is adapted for selectively ablating an isthmus of the heart upon supply of an ablation medium to the ablation element by an ablation source.

6. The ablation device according to claim 5, wherein the ablation element comprises a shape memory material in which a predefined shape is stored.

7. The ablation device according to claim 5, wherein the ablation catheter comprises a folding mechanism adapted for being actuable via an ablation control handle part to fold the ablation element into a defined folded configuration in which at least a part of the folded ablation element abuts against the isthmus.

8. The ablation device according to claim 5, wherein the ablation element is convertible between a straight configuration and a bent configuration by actuating an ablation control handle part.

9. The ablation device according to claim 8, wherein the bent configuration of the ablation element follows an anatomical isthmus shape.

10. The ablation device according to claim 1, comprising a common sleeve accommodating a part of the positioning catheter and a part of the ablation catheter.

11. The ablation device according to claim 10, wherein the sleeve has a first lumen in which the part of the positioning catheter is accommodated and has a second lumen in which the part of the ablation catheter is accommodated.

12. The ablation device according to claim 1, wherein the tubular body has a spatially varying wall thickness along the circumference of the tubular body.

13. The ablation device according to claim 1, wherein the tubular body has a spatially varying material composition along the circumference of the tubular body.

14. The ablation device according to claim 1, wherein the tubular body has a first portion having a minimum value of thermal conductivity along the circumference of the tubular body and has a second portion having a maximum value of thermal conductivity along the circumference of the tubular body, and wherein the first portion and the second portion are arranged to oppose one another along the circumference.

15. The ablation device according to claim 14, wherein the spatial dependence of the thermal conductivity along the circumference of the tubular body is axially symmetric with regard to a mirror axis formed by a center of the first portion and by a center of the second portion.

16. The ablation device according to claim 1, wherein the tubular body is configured to have a gradually varying, and continuously differentiable, value of thermal conductivity along the circumference of the tubular body.

17. The ablation device according to claim 1, wherein the tubular body comprises a core formed by a wound filament structure of a metal braiding or metal coiling, and comprises a mantle formed by a plastic material surrounding the core.

18. The ablation device according to claim 17, wherein the tubular body comprises a liner lining an inner surface of the core.

19. A method of operating an ablation device, comprising the steps of:
    positioning a positioning catheter of the ablation device in a heart and fixing the positioning catheter in the heart by a fixation mechanism;
    recording signals by electrodes of the positioning catheter, wherein the electrodes are arranged proximal from the fixation mechanism along an extension of the positioning catheter, wherein a portion of the extension is abutable against the isthmus;
    analyzing the signals for positioning a slidable ablation applicator of an ablation catheter along the positioning catheter such that an isthmus can be ablated;
    guiding the ablation catheter via sleeves at the positioning catheter and forming a continuous elongated lesion; and
    ablating tissue selectively along the isthmus of the heart using the ablation catheter of the ablation device;
    wherein the method of operating further comprises moving the positioning catheter and the ablation catheter relative to one another;
    wherein the ablation element comprises a tubular body defining an inner lumen; and
    wherein the tubular body is configured to have a spatially varying value of thermal conductivity along a circumference of the tubular body.

20. An ablation device, the ablation device comprising:
    a positioning catheter adapted to be positionable in a heart and comprising a fixation mechanism for fixing the positioning catheter in the heart;
    an ablation catheter adapted to ablate material of the heart using the ablation catheter;

wherein the ablation device is designed to ablate tissue selectively along an isthmus of the heart;

wherein the positioning catheter and the ablation catheter are provided to be movable relative to one another;

wherein the ablation catheter can be guided via sleeves at the positioning catheter; and wherein the positioning catheter comprises electrodes for recording signals to be analyzed for positioning a slidable ablation element of the ablation catheter along the positioning catheter such that the isthmus can be ablated;

wherein the ablation element is adapted for selectively ablating an isthmus of the heart upon supply of an ablation medium to the ablation element by an ablation source; and wherein the ablation element comprises:

a tubular body defining an inner lumen; and wherein the tubular body is configured to have a spatially varying value of thermal conductivity along a circumference of the tubular body.

* * * * *